United States Patent
Ishibashi et al.

(10) Patent No.: US 9,570,540 B2
(45) Date of Patent: *Feb. 14, 2017

(54) NITRIDE CRYSTAL, NITRIDE CRYSTAL SUBSTRATE, EPILAYER-CONTAINING NITRIDE CRYSTAL SUBSTRATE, SEMICONDUCTOR DEVICE AND METHOD OF MANUFACTURING THE SAME

(71) Applicant: SUMITOMO ELECTRIC INDUSTRIES, LTD., Osaka (JP)

(72) Inventors: Keiji Ishibashi, Hyogo (JP); Tokiko Kaji, Hyogo (JP); Seiji Nakahata, Hyogo (JP); Takayuki Nishiura, Hyogo (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 292 days.

This patent is subject to a terminal disclaimer.

(21) Appl. No.: 14/455,781

(22) Filed: Aug. 8, 2014

(65) Prior Publication Data
US 2014/0349112 A1 Nov. 27, 2014

Related U.S. Application Data

(60) Continuation of application No. 13/935,360, filed on Jul. 3, 2013, now Pat. No. 8,828,140, which is a (Continued)

(30) Foreign Application Priority Data

Jun. 23, 2005 (JP) .................................. 2005-183111

(51) Int. Cl.
*C30B 25/14* (2006.01)
*H01L 29/04* (2006.01)
(Continued)

(52) U.S. Cl.
CPC ................ *H01L 29/04* (2013.01); *C30B 29/38* (2013.01); *C30B 29/403* (2013.01); *C30B 33/00* (2013.01);
(Continued)

(58) Field of Classification Search
CPC ....... C30B 29/403; C30B 25/14; C30B 29/406
See application file for complete search history.

(56) References Cited

U.S. PATENT DOCUMENTS 5,679,152 A 10/1997 Tischler et al.
5,679,153 A 10/1997 Dmitriev et al.
(Continued)

FOREIGN PATENT DOCUMENTS

CN 1610138 A 4/2005
CN 1896343 A 1/2007
(Continued)

OTHER PUBLICATIONS

Taiwan Office Action issued in Taiwanese Patent Application No. 095122536 dated Jul. 10, 2012.
(Continued)

*Primary Examiner* — Robert M Kunemund
(74) *Attorney, Agent, or Firm* — McDermott Will & Emery LLP

(57) ABSTRACT

A nitride crystal is characterized in that, in connection with plane spacing of arbitrary specific parallel crystal lattice planes of the nitride crystal obtained from X-ray diffraction measurement performed with variation of X-ray penetration depth from a surface of the crystal while X-ray diffraction conditions of the specific parallel crystal lattice planes are satisfied, a uniform distortion at a surface layer of the crystal represented by a value of $|d_1-d_2|/d_2$ obtained from the plane spacing $d_1$ at the X-ray penetration depth of 0.3 μm and the plane spacing $d_2$ at the X-ray penetration depth of 5 μm is
(Continued)

equal to or lower than $2.1 \times 10^{-3}$. The above configuration provides the nitride crystal having a crystal surface layer that is evaluated directly and reliably without breaking the crystal so that it can be used in a preferred fashion as a substrate for a semiconductor device as well as the nitride crystal substrate, an epilayer-containing nitride crystal substrate, a semiconductor device and a method of manufacturing the same.

8 Claims, 3 Drawing Sheets

Related U.S. Application Data continuation of application No. 12/635,490, filed on Dec. 10, 2009, now abandoned, which is a continuation of application No. 12/216,236, filed on Jul. 1, 2008, now Pat. No. 7,854,804, which is a division of application No. 11/473,122, filed on Jun. 23, 2006, now Pat. No. 7,416,604.

(51) Int. Cl.
*C30B 29/40* (2006.01)
*C30B 33/00* (2006.01)
*H01L 29/20* (2006.01)
*C30B 29/38* (2006.01)

(52) U.S. Cl.
CPC ......... *H01L 29/045* (2013.01); *H01L 29/2003* (2013.01); *Y10T 428/2978* (2015.01)

(56) References Cited

U.S. PATENT DOCUMENTS

| | | |
|---|---|---|
| 6,280,523 B1 | 8/2001 | Coman et al. |
| 6,396,083 B1 | 5/2002 | Ortiz et al. |
| 6,458,013 B1 | 10/2002 | Saka |
| 6,488,767 B1 | 12/2002 | Xu et al. |
| 6,596,079 B1 | 7/2003 | Vaudo et al. |
| 6,656,615 B2 | 12/2003 | Dwilinski et al. |
| 6,841,274 B2 | 1/2005 | Ueno et al. |
| 6,875,544 B1 | 4/2005 | Sweatt et al. |
| 6,951,695 B2 | 10/2005 | Xu et al. |
| 7,416,604 B2 | 8/2008 | Ishibashi et al. |
| 7,421,060 B2 | 9/2008 | Zienert et al. |
| 7,854,804 B2 | 12/2010 | Ishibashi et al. |
| 8,828,140 B2 * | 9/2014 | Ishibashi ............... C30B 29/403 117/101 |
| 2002/0028564 A1 | 3/2002 | Motoki et al. |
| 2002/0192507 A1 | 12/2002 | Dwilinski et al. |
| 2005/0082564 A1 | 4/2005 | Kitaoka et al. |
| 2006/0035910 A1 | 2/2006 | Lochead et al. |
| 2006/0236922 A1 | 10/2006 | Ishibashi et al. |
| 2006/0237740 A1 | 10/2006 | Bousquet et al. |
| 2006/0272572 A1 | 12/2006 | Uematsu et al. |
| 2006/0273343 A1 | 12/2006 | Nakahata et al. |
| 2006/0292728 A1 | 12/2006 | Ishibashi et al. |
| 2007/0281484 A1 | 12/2007 | Ishibashi et al. |
| 2008/0056449 A1 | 3/2008 | Zienert et al. |
| 2008/0057608 A1 | 3/2008 | Ishibashi et al. |
| 2008/0232416 A1 | 9/2008 | Okamoto et al. |
| 2008/0271667 A1 | 11/2008 | Ishibashi et al. |
| 2008/0272392 A1 | 11/2008 | Ishibashi et al. |
| 2008/0283846 A1 | 11/2008 | Ohmae et al. |
| 2008/0283851 A1 | 11/2008 | Akita |
| 2008/0308906 A1 | 12/2008 | Osada et al. |
| 2009/0104738 A1 | 4/2009 | Ring et al. |
| 2009/0155989 A1 | 6/2009 | Uematsu et al. |
| 2010/0224963 A1 | 9/2010 | Ishibashi et al. |
| 2010/0227532 A1 | 9/2010 | Ishibashi et al. |
| 2010/0230690 A1 | 9/2010 | Kyono et al. |
| 2011/0031589 A1 | 2/2011 | Ishibashi |
| 2011/0057200 A1 | 3/2011 | Kyono et al. |
| 2011/0084363 A1 | 4/2011 | Ishibashi et al. |
| 2011/0223701 A1 | 9/2011 | Kyono et al. |

FOREIGN PATENT DOCUMENTS

| | | |
|---|---|---|
| CN | 101350333 A | 1/2009 |
| CN | 101409231 A | 4/2009 |
| EP | 1 365 230 A2 | 11/2003 |
| EP | 1 717 286 A1 | 11/2006 |
| EP | 1 736 574 A1 | 12/2006 |
| EP | 1863074 A2 | 12/2007 |
| EP | 1897978 A1 | 3/2008 |
| JP | 5-087646 A | 4/1993 |
| JP | 6-066740 A | 3/1994 |
| JP | 10-256662 A | 9/1998 |
| JP | 2001-36191 A | 2/2001 |
| JP | 2001-322899 A | 11/2001 |
| JP | 2002-029897 A | 1/2002 |
| JP | 2002-289579 A | 10/2002 |
| JP | 2003-112999 A | 4/2003 |
| JP | 2004-193371 A | 7/2004 |
| JP | 2004-530306 A | 9/2004 |
| JP | 2004-281671 A | 10/2004 |
| JP | 2004-311575 A | 11/2004 |
| JP | 2006-71354 A | 3/2006 |
| JP | 2006-310362 A | 11/2006 |
| JP | 2007-005526 A | 1/2007 |
| JP | 2008-010835 A | 1/2008 |
| JP | 2008-235802 A | 10/2008 |
| JP | 2008-285364 A | 11/2008 |
| JP | 2009-170798 A | 7/2009 |
| JP | 4305574 B1 | 7/2009 |
| JP | 2009-200437 A | 9/2009 |
| JP | 4333820 B1 | 9/2009 |
| JP | 2009-238772 A | 10/2009 |
| JP | 4375497 B1 | 12/2009 |
| JP | 4518209 B1 | 8/2010 |
| WO | 0168955 A1 | 9/2001 |
| WO | 02/101121 A1 | 12/2002 |
| WO | 2005/041283 A1 | 5/2005 |

OTHER PUBLICATIONS

Japanese Notice of Grounds of Rejection, w/ English translation thereof, issued in Japanese Patent Application No. JP 2009-287590 dated May 24, 2011.

Japanese Notice of Grounds of Rejection, w/ English translation thereof, issued in Japanese Patent Application No. JP 2009-287590 dated Jul. 12, 2011.

Japanese Decision to Grant Patent, w/ English translation thereof, issued in Japanese Patent Application No. JP 2009-287590 dated Aug. 30, 2011.

International Search Report issued in International Patent Application No. PCT/JP2010/068840 dated Jan. 25, 2011.

International Search Report issued in International Patent Application No. PCT/JP2010/070290 dated Dec. 14, 2010.

Korean Office Action issued in Korean Patent Application No. KR 10-2011-0138617 dated Apr. 3, 2012.

Japanese Office Action, with English translation, issued in Japanese Patent Application No. 2010-117702, dated Mar. 27, 2012.

Japanese Office Action, with English translation, issued in Japanese Patent Application No. 2008-334503, dated Jul. 12, 2011.

US Office Action issued in U.S. Appl. No. 12/216,237, dated Jul. 1, 2011.

Chinese Office Action, w/ English translation thereof, issued in Chinese Patent Application No. CN 200610093296.1 dated May 16, 2011.

United States Notice of Allowance issued in U.S. Appl. No. 12/216,236 dated Sep. 7, 2010.

United States Office Action issued in U.S. Appl. No. 12/635,490 dated Mar. 4, 2013.

Entire Prosecution of U.S. Appl. No. 12/216,635,490 filed on Oct. 12, 2009 to Hiroshi Komori entitled "Nitride Crystal, Nitride

(56) References Cited

OTHER PUBLICATIONS

Crystal Substrate, Epilayer-Containing Nitride Crystal Substrate, Semiconductor Device and Method of Manufacturing the Same".
Sung S. Park, et al., "Free-Standing GaN Substrates by Hydride Vapor Phase Epitaxy," Jpn J. Appl. Phys., Nov. 15, 2000, pp. L1141-L1142, vol. 39, The Japan Society of Applied Physics.
Yutaka Takahashi, et al., "Transmission Electron Microscopy of Surface Damages Resulting from Wet Polishing in a Polycrystalline Aluminum Nitride Substrate," The Academic Journal of the Ceramic Society of Japan, 1991, pp. 613-619, 99[7], The Ceramic Society of Japan.
Entire Prosecution of U.S. Appl. No. 11/473,122 filed on Jun. 23, 2006 to Hiroshi Komori entitled "Nitride Crystal, Nitride Crystal Substrate, Epilayer-Containing Nitride Crystal Substrate, Semiconductor Device and Method of Manufacturing the Same".
Japanese Notice of Grounds of Rejection, w/ English translation thereof, issued in Japanese Patent Application No. JP 2009-064672 dated Apr. 21, 2009.
Japanese Notice of Grounds of Rejection, w/ English translation thereof, issued in Japanese Patent Application No. JP 2009-170813 dated Aug. 25, 2009.
United States Office Action issued in U.S. Appl. No. 12/216,237, mailed Mar. 19, 2010.
Notice of Grounds of Rejection, with English translation, issued in Japanese Patent Application No. 2009-287970, mailed Mar. 9, 2010.
International Search Report, with English translation, issued in International Patent Application No. PCT/JP2010/051158, mailed Feb. 23, 2010.
U.S. Office Action issued in U.S. Appl. No. 12/216,237, mailed Apr. 27, 2009.
Japanese Office Action issued in Application No. 2012-137811 dated Jun. 25, 2013.
Extended European Search Report issued in Euroepan Application No. 10837390.3 dated Oct. 10, 2013.
Japanese Notice of Grounds of Rejection, w/ English translation thereof, issued in Japanese Patent Application No. JP 2005-183111 dated on Oct. 28, 2008.
United States Office Action issued in U.S. Appl. No. 12/216,237 dated Oct. 29, 2009.
United States Office Action issued in U.S. Appl. No. 12/216,236 mailed Mar. 25, 2010.
United States Office Action issued in U.S. Appl. No. 13/935,360 mailed Dec. 6, 2013.
United States Notice of Allowance issued in U.S. Appl. No. 13/935,360 mailed May 2, 2014.
Chinese Office Action issued in Chinese Application No. 201080039771.1 dated Jan. 30, 2014, with English Abstract.
Japanese Notice of Grounds of Rejection, w/English translation thereof, issued in Japanese Patent Application No. JP 2005-183111 dated Oct. 28, 2008.
United States Office Action issued in U.S. Appl. No. 12/837,872 mailed Sep. 20, 2013.
Entire Prosecution of U.S. Appl. No. 12/216,236, filed on Jul. 1, 2008 to Hiroshi Komori entitled "Nitride Crystal, Nitride Crystal Substrate, Epilayer-Containing Nitride Crystal Substrate, Semiconductor Device and Method of Manufacturing the Same".
USPTO. 2015. Office Action, issued Sep. 4, 2015 for U.S. Appl. No. 13/526,061, entitled "Group III Nitride Crystal Substrate, Epilayer-Containing Group ii Nitride Crystal Substrate, Semiconductor Device and Method of Manufacturing the Same."

* cited by examiner

US 9,570,540 B2

NITRIDE CRYSTAL, NITRIDE CRYSTAL SUBSTRATE, EPILAYER-CONTAINING NITRIDE CRYSTAL SUBSTRATE, SEMICONDUCTOR DEVICE AND METHOD OF MANUFACTURING THE SAME

CROSS REFERENCE TO RELATED APPLICATIONS

This application is a U.S. Continuation of U.S. patent application Ser. No. 13/935,360, filed on Jul. 3, 2013 now U.S. Pat. No. 8,828,140, which is the U.S. Continuation Application of U.S. application Ser. No. 12/635,490, filed on Dec. 10, 2009, now abandoned which is a Continuation Application of U.S. application Ser. No. 12/216,236, filed on Jul. 1, 2008, now U.S. Pat. No. 7,854,804, which is a Division Application of U.S. application Ser. No. 11/473, 122, filed on Jun. 23, 2006, now U.S. Pat. No. 7,416,604, which in turn claims the benefit of Japanese Application No. 2005-183111, filed on Jun. 23, 2005, the disclosures of which Applications are incorporated by reference herein.

BACKGROUND OF THE INVENTION

Field of the Invention

The present invention relates to a nitride crystal, a nitride crystal substrate, an epilayer-containing nitride crystal substrate, a semiconductor device and a method of manufacturing the same, and particularly to a nitride crystal that can be preferably used as a substrate for growing an epitaxial crystal when producing a semiconductor device.

Description of the Background Art

As is well known, various devices using nitride semiconductor crystals have been produced in recent years, and nitride semiconductor light emitting devices have been produced as a typical example of such semiconductor devices.

Generally, in a process of manufacturing a nitride semiconductor device, a plurality of nitride semiconductor layers are epitaxially grown on a substrate. Crystal quality of the epitaxially grown nitride semiconductor layer is affected by a state of a surface layer of the substrate used for the epitaxial growth, and this quality affects performance of the semiconductor device including the nitride semiconductor layer. Therefore, in the case where the nitride semiconductor crystal is used as the above kind of substrate, it is desired that at least a main surface of the substrate providing a base of epitaxial growth has a smooth form without a distortion.

More specifically, the main surface of the nitride semiconductor substrate used for the epitaxial growth is generally subjected to smoothing processing and distortion removal processing. Among various compound semiconductors, gallium-nitride-based semiconductors are relatively hard so that the surface smoothing processing thereof is not easy, and the distortion removal processing after the smoothing processing is not easy.

Japanese Patent Laying-Open No. 2004-311575 has disclosed a polishing method that uses soft grains and hard grains as polishing compounds for polishing a surface of a nitride gallium substrate. U.S. Pat. No. 6,596,079 has disclosed a method of forming a substrate surface in the case where the substrate is produced from an (AlGaIn)N bulk crystal grown by vapor phase epitaxy on an (AlGaIn)N seed crystal, and more specifically a method of forming a substrate surface that has a RMS (Root Mean Square) surface roughness of 1 nm or lower, and does not have a surface damage owing to effecting CMP (Chemical-Mechanical Polishing) or etching on the substrate surface subjected to mechanical polishing. U.S. Pat. No. 6,488,767 has disclosed an $Al_xGa_yIn_zN$ ($0<y\leq1$, $x+y+z=1$) substrate having an RMS surface roughness of 0.15 nm attained by the CMP processing. A processing agent for this CMP contains $Al_2O_3$ grains, $SiO_2$ grains, pH controlling agent and oxidizer. According to Japanese Patent Laying-Open No. 2001-322899, a work-affected layer is removed by dry etching to finish the substrate surface after polishing the GaN substrate.

In the prior art, as described above, the CMP processing or dry etching is effected after mechanically polishing the GaN crystal so that the work-affected layer formed by the mechanical polishing is removed, and the GaN substrate having the finished substrate surface is formed. However, the processing rate of the CMP processing is low, and causes problems in cost and productivity. Further, the dry etching causes a problem in surface roughness.

The finishing method of the Si substrate using the CMP as well as the polishing agent for the method are not suitable for the hard nitride semiconductor substrate, and lower the removal speed of the surface layer. In particular, GaN is chemically suitable, and is relatively resistant to the wet etching so that the CMP processing is not easy. Although the dry etching can remove the nitride semiconductor surface, it does not have an effect of flattening the surface in a horizontal direction so that the surface smoothing effect cannot be achieved.

For epitaxially growing the compound semiconductor layer of good crystal quality on the substrate surface, it is necessary to use the substrate surface having good crystal quality as well as less work damage and less distortion as described above. However, the crystal quality of the surface layer that is required at the substrate surface is not clear.

In the prior art, distortions at the surface layer of the crystal are evaluated by cleaving the crystal, and observing the cleavage plane with a TEM (Transmission Electron Microscope) as disclosed, e.g., in S. S. Park et al, "Free-Standing GaN Substrate by Hydride Vapor Phase Epitaxy", Jpn, J. Appl. Phys., The Japan Society of Applied Physics, Vol. 39, November 2000, pp. L1141-L1142 and Yutaka TAKAHASHI et al, "Transmission Electron Microscopy of Surface Damages Resulting from Wet Polishing in a Polycrystalline Aluminum Nitride Substrate", The Academic Journal of the Ceramic Society of Japan, The Ceramic Society of Japan, 99, [7], (1991), pp. 613-619. Thus, the distortions at the surface layer of the crystal have conventionally been evaluated by a breaking test that breaks the crystal, and therefore such problems occur that correction cannot be performed after the evaluation even when the result of evaluation was insufficient, and that the evaluation cannot be effected on the product in itself. Under the present circumstances, there is no index for nondestructively evaluating the crystallinity of the surface layer at the finished substrate surface, and it is difficult to define quantitatively the crystal quality of the surface layer.

SUMMARY OF THE INVENTION

An object of the invention is to provide a nitride crystal, a nitride crystal substrate having a crystal surface layer that is evaluated directly and reliably without breaking the crystal so that it can be used in a preferred fashion as a substrate for epitaxial crystal growth when producing a semiconductor device, as well as an epilayer-containing nitride crystal substrate, a semiconductor device and a method of manufacturing the same.

According to an aspect of the invention, a nitride crystal is characterized in that, in connection with plane spacing of arbitrary specific parallel crystal lattice planes of the nitride crystal obtained from X-ray diffraction measurement performed with variation of X-ray penetration depth from a surface of the crystal while X-ray diffraction conditions of the specific parallel crystal lattice planes are satisfied, a uniform distortion at a surface layer of the crystal represented by a value of $|d_1-d_2|/d_2$ obtained from the plane spacing $d_1$ at the X-ray penetration depth of 0.3 μm and the plane spacing $d_2$ at the X-ray penetration depth of 5 μm is equal to or lower than $2.1 \times 10^{-3}$.

According to another aspect of the invention, a nitride crystal is characterized in that, on a diffraction intensity profile of arbitrary specific parallel crystal lattice planes of the nitride crystal obtained from X-ray diffraction measurement performed with variation of X-ray penetration depth from a surface of the crystal while X-ray diffraction conditions of the specific parallel crystal lattice planes are satisfied, an irregular distortion at a surface layer of the crystal represented by a value of $|v_1-v_2|$ obtained from a half value width $v_1$ of a diffraction intensity peak at the X-ray penetration depth of 0.3 μm and a half value width $v_2$ of the diffraction intensity peak at the X-ray penetration depth of 5 μm is equal to or lower than 150 arcsec.

According to still another aspect of the invention, a nitride crystal is characterized in that, on a rocking curve measured by varying an X-ray penetration depth from a crystal surface in connection with X-ray diffraction of arbitrary specific parallel crystal lattice planes of the nitride crystal, a plane orientation deviation of the specific parallel crystal lattice planes represented by a value of $|w_1-w_2|$ obtained from a half value width $w_1$ of a diffraction intensity peak at the X-ray penetration depth of 0.3 μm and a half value width $w_2$ of the diffraction intensity peak at the X-ray penetration depth of 5 μm is equal to or lower than 400 arcsec.

Preferably, the surface of the nitride crystal has a surface roughness Ry of 30 nm or lower. It is also preferable that the surface of the nitride crystal has the surface roughness Ry of 3 nm or lower.

Preferably, the surface of the nitride crystal is parallel to a C-plane of a wurtzite structure. It is also preferable that the surface of the nitride crystal has an off angle in a range from 0.05° to 15° with respect to a C-plane of a wurtzite structure.

A nitride crystal substrate formed of the nitride crystal described above is preferable as a substrate for a semiconductor device. An epilayer-containing nitride crystal substrate including one or more semiconductor layer(s) formed by epitaxial growth on at least one of main surface sides of the nitride crystal substrate is also preferable as the substrate for the semiconductor device. The epilayer is one or more semiconductor layer(s) formed by epitaxial growth on at least one of the main surface sides of the nitride crystal substrate.

According to still another aspect of the invention, a semiconductor device is a semiconductor device including the nitride crystal substrate or the epilayer-containing nitride crystal substrate described above as the substrate. The semiconductor device of this aspect includes one or more semiconductor layer(s) formed by epitaxial growth on at least one of the main surface sides of the substrate.

According to a yet another aspect of the invention, a semiconductor device is a semiconductor device including the nitride crystal substrate or the epilayer-containing nitride crystal substrate described above as the substrate. The semiconductor device of this aspect includes a light-emitting element including three or more semiconductor layers formed by epitaxial growth on one of the main surface sides of the substrate, a first electrode formed on the other main surface side of the nitride crystal substrate or the epilayer-containing nitride crystal substrate, and a second electrode formed on the outermost semiconductor layer among the plurality of semiconductor layers, and further includes a conductor bearing the light-emitting element. Further, the semiconductor device of this aspect is configured such that a side of the substrate of the light emitting element is has a light emitting side and the outermost semiconductor layer side is a mount side, and the plurality of semiconductor layers include a p-type semiconductor layer, an n-type semiconductor layer and a light emitting layer formed between these conductive semiconductor layers.

According to a further aspect of the invention, a method of manufacturing a semiconductor device is a method of manufacturing a semiconductor device including, as a substrate, a nitride crystal substrate or an epilayer-containing nitride crystal substrate including one or more semiconductor layer(s) formed by epitaxial growth on at least one of main surface sides of the nitride crystal substrate. The method selects, as the nitride crystal substrate, nitride crystal configured such that, in connection with plane spacing of arbitrary specific parallel crystal lattice planes of the crystal obtained from X-ray diffraction measurement performed with variation of X-ray penetration depth from a surface of the crystal while X-ray diffraction conditions of the specific parallel crystal lattice planes are satisfied, a uniform distortion at a surface layer of the crystal represented by a value of $|d_1-d_2|/d_2$ obtained from the plane spacing $d_1$ at the X-ray penetration depth of 0.3 μm and the plane spacing $d_2$ at the X-ray penetration depth of 5 μm is equal to or lower than $2.1 \times 10^{-3}$. Further, the method of manufacturing the semiconductor of this aspect includes a step of epitaxially growing one or more semiconductor layer(s) on at least one of main surface sides of the substrate.

According to a further aspect of the invention, a method of manufacturing a semiconductor device is a method of manufacturing a semiconductor device including, as a substrate, a nitride crystal substrate or an epilayer-containing nitride crystal substrate including one or more semiconductor layer(s) formed by epitaxial growth on at least one of main surface sides of the nitride crystal substrate. The method selects, as the nitride crystal substrate, nitride crystal configured such that, on a diffraction intensity profile of arbitrary specific parallel crystal lattice planes of the nitride crystal obtained from X-ray diffraction measurement performed with variation of X-ray penetration depth from a surface of the crystal while X-ray diffraction conditions of the specific parallel crystal lattice planes are satisfied, an irregular distortion at a surface layer of the crystal represented by a value of $|v_1-v_2|$ obtained from a half value width $v_1$ of a diffraction intensity peak at the X-ray penetration depth of 0.3 μm and a half value width $v_2$ of the diffraction intensity peak at the X-ray penetration depth of 5 μm is equal to or lower than 150 arcsec. Further, the method of manufacturing the semiconductor of this aspect includes a step of epitaxially growing one or more semiconductor layer(s) on at least one of main surface sides of the substrate.

According to a further aspect of the invention, a method of manufacturing a semiconductor device is a method of manufacturing a semiconductor device including, as a substrate, a nitride crystal substrate or an epilayer-containing nitride crystal substrate including one or more semiconductor layer(s) formed by epitaxial growth on at least one of main surface sides of the nitride crystal substrate. The method selects, as the nitride crystal substrate, nitride crystal configured such that, on a rocking curve measured by varying an X-ray penetration depth from a crystal surface in connection with X-ray diffraction of arbitrary specific parallel crystal lattice planes of the nitride crystal, a plane orientation deviation of the specific parallel crystal lattice planes represented by a value of $|w_1-w_2|$ obtained from a half value width $w_1$ of a diffraction intensity peak at the X-ray penetration depth of 0.3 μm and a half value width $w_2$ of the diffraction intensity peak at the X-ray penetration depth of 5 μm is equal to or lower than 400 arcsec. Further, the method of manufacturing the semiconductor of this aspect includes a step of epitaxially growing one or more semiconductor layer(s) on at least one of main surface sides of the substrate.

The invention can provide the nitride crystal having a crystal surface layer that is evaluated directly and reliably without breaking the crystal so that it can be used in a preferred fashion as a substrate for epitaxial crystal growth when producing a semiconductor device as well as the nitride crystal substrate, the epilayer-containing nitride crystal substrate, the semiconductor device and the method of manufacturing the same.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The invention employs an X-ray diffraction method, and thereby can perform direct evaluation of crystallinity at a surface layer of a nitride crystal without breaking the crystal. The evaluation of the crystallinity represents evaluation or determination of an extent or degree to which a distortion of the crystal is present, and more specifically represents evaluation of an extent or degree to which a distortion of a crystal lattice and a plane orientation deviation of the lattice plane are present. The distortion of the crystal lattice can be specifically classified into a uniform distortion caused by a uniformly distorted crystal lattice and an irregular distortion caused by an irregularly distorted crystal lattice. The plane orientation deviation of the crystal lattice planes represent a magnitude by which the plane orientation of the lattice plane of each crystal region deviates from an average orientation of the plane orientation of the lattice planes of the whole crystal lattice.

Figure 1:
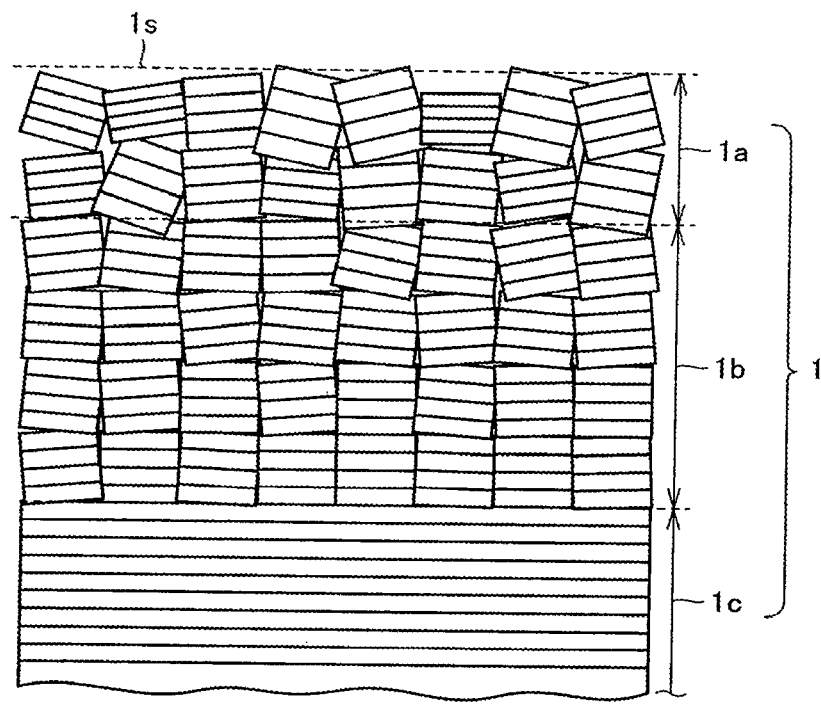
FIG. 1 is a schematic section showing a state of a crystal in a depth direction from a crystal surface.

As shown in FIG. 1, a nitride crystal 1 has a crystal surface layer 1a having a certain depth from a crystal surface 1s, and this crystal surface layer 1a has a uniform distortion, an irregular distortion and/or a plane orientation deviation of a crystal lattice occur in crystal surface layer 1a due to working such as cutting, grinding or polishing. The uniform distortion, irregular distortion and/or plane orientation deviation of the crystal lattice may occur in a surface-neighboring layer 1b neighboring to crystal surface layer 1a (FIG. 1 shows a case where the plane orientation deviation of the crystal lattice is present. Further, it can be considered that a crystal inner layer 1c located inside surface-neighboring layer 1b has an original crystal structure of the crystal. The states and thicknesses of crystal surface layer 1a and surface-neighboring layer 1b depend on the manner and extent of the grinding or polishing in the surface working processing.

In the above structure, the uniform distortion, irregular distortion and/or plane direction deviation of the crystal lattice are evaluated in the depth direction from the surface of the crystal so that the crystallinity of the crystal surface layer can be directly and reliably evaluated.

In the X-ray diffraction measurement for evaluating the crystallinity of the surface layer of the nitride crystal according to the invention, an X-ray penetration depth from the surface of the crystal is changed while X-ray diffraction conditions of arbitrary specific parallel crystal lattice planes of the nitride crystal are satisfied.

The diffraction conditions of the arbitrary specific parallel crystal lattice planes represent conditions under which the arbitrarily specified parallel crystal lattice planes diffracts the X-ray. Assuming that a Bragg angle is θ, a wavelength of the X-ray is λ and a plane spacing of the crystal lattice planes is d, the X-ray is diffracted by the crystal lattice plane satisfying the Bragg's condition (2d sin θ=nλ, where n is an integer).

Figure 2:
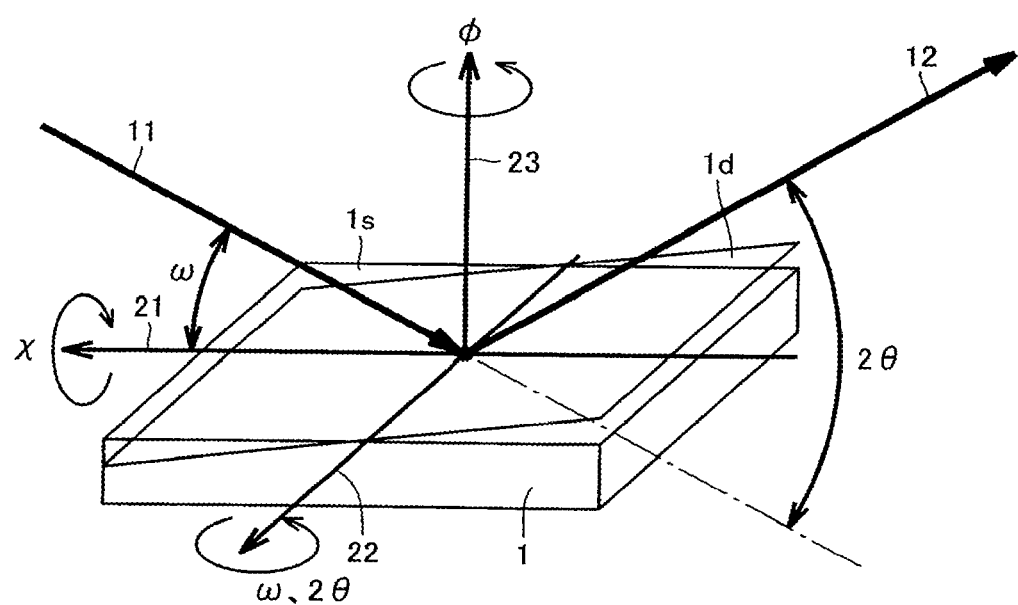
FIG. 2 is a schematic view showing measurement axes and measurement angles in an X-ray diffraction method according to the invention.

The X-ray penetration depth represents a distance that is measured in the depth direction perpendicular to crystal surface 1s, and causes an intensity of the incident X-ray equal to 1/e where e is a base of the natural logarithm. Referring to FIG. 2, an X-ray linear absorption coefficient μ of crystal 1, an inclination angle χ of crystal surface 1s, an X-ray incident angle ω with respect to crystal surface 1s and a Bragg angle θ in crystal surface is determines X-ray penetration depth T that is expressed by an equation (1). A φ represents a rotation angle in crystal surface. A χ axis 21 is present on a plane formed by an incident X-ray 11 and an outgoing X-ray 12, a ω axis (2θ axis) 22 is perpendicular to a plane formed by incident X-ray 11 and outgoing X-ray 12, and a φ axis 23 is perpendicular to crystal surface 1s.

$$T = \frac{1}{\mu} \cdot \frac{\cos \chi \cdot \sin \omega \cdot \sin(2\theta - \omega)}{\sin \omega + \sin(2\theta - \omega)} \quad (1)$$

Therefore, X-ray penetration depth T can be continuously changed by adjusting at least one of χ, ω and φ to satisfy the diffraction conditions for the above specific crystal lattice planes.

For continuously changing X-ray penetration depth T to satisfy the diffraction conditions for a specific crystal lattice plane 1$d$, it is necessary that specific crystal lattice plane 1$d$ is not parallel to crystal surface 1$s$. If specific crystal lattice plane 1$d$ is parallel to crystal surface 1$s$, the angle θ between crystal lattice plane 1$d$ and incident X-ray 11 becomes equal to angle ω between crystal surface 1$s$ and incident X-ray 11 so that the X-ray penetration depth cannot be changed at specific crystal lattice plane 1$d$.

Based on the following embodiment, description will now be given on the evaluation performed in such a manner that the arbitrary specific parallel crystal lattice planes of the crystal is irradiated with the X-ray while changing the X-ray penetration depth, the uniform distortion of the crystal lattice is evaluated from the change in plane spacing on the diffraction profile relating to this specific parallel crystal lattice planes, the irregular distortion of the crystal lattice is evaluated from the change in half value width of the diffraction peak on the diffraction profile and the plane orientation deviation of the crystal lattice is evaluated from the change in half value width on the rocking curve.

First Embodiment

A nitride crystal of this embodiment is characterized in that, in connection with plane spacing of arbitrary specific parallel crystal lattice planes of the crystal obtained from X-ray diffraction measurement performed with variation of X-ray penetration depth from a surface of the crystal while X-ray diffraction conditions of the specific parallel crystal lattice planes are satisfied, a uniform distortion at a surface layer of the crystal represented by a value of $|d_1-d_2|/d_2$ obtained from a plane spacing $d_1$ at the X-ray penetration depth of 0.3 μm and a plane spacing $d_2$ at the X-ray penetration depth of 5 μm is equal to or lower than $2.1\times10^{-3}$.

Figure 3:
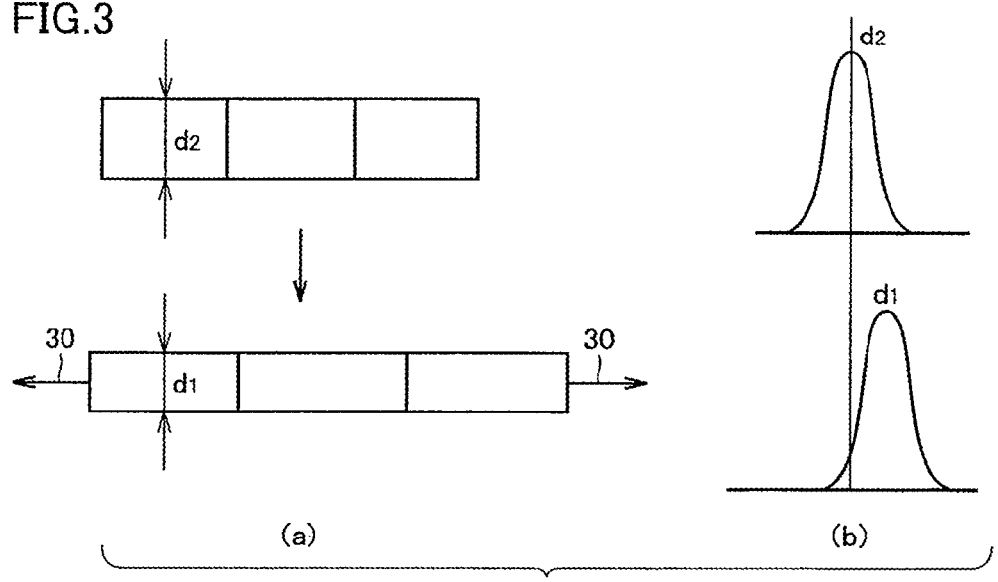
FIG. 3 schematically illustrates a relationship between a uniform distortion of a crystal lattice of a nitride crystal and plane spacing of specific parallel crystal lattice planes is shown on a diffraction profile in the X-ray diffraction method. At (a), the uniform distortion of the crystal lattice is illustrated. At (b), the plane spacing of the specific parallel crystal lattice plane is shown on the diffraction profile.

Referring to FIG. 1, the X-ray penetration depth of 0.3 μm corresponds to a distance from the surface of the nitride crystal to an inside of crystal surface layer 1$a$, and the X-ray penetration depth of 5 μm corresponds to a distance from the surface of the nitride crystal to an inside of crystal inner layer 1$c$. Referring to FIG. 3($a$), plane spacing $d_2$ at the X-ray penetration depth of 5 μm can be considered as the plane spacing of the specific parallel crystal lattice planes of the nitride crystal in the original state, but plane spacing $d_1$ at the X-ray penetration depth of 0.3 μm reflects the uniform distortion of the crystal lattice at the crystal surface layer due to an influence (e.g., a tensile stress 30 toward an inside of the crystal lattice plane) of surface working of the crystal, and therefore takes a value different from plane spacing $d_2$ at the X-ray penetration depth of 5 μm.

Referring to FIG. 3($b$), plane spacing $d_1$ at the X-ray penetration depth of 0.3 μm and plane spacing $d_2$ at the X-ray penetration depth of 5 μm appear on the diffraction profile relating to the arbitrary specific parallel crystal lattice planes of the crystal in the above case. Therefore, the uniform distortion of the crystal surface layer can be expressed by the value of a ratio $|d_1-d_2|/d_2$ of a difference between $d_1$ and $d_2$ with respect to $d_2$.

In the nitride crystal of this embodiment, the uniform distortion at the surface layer represented by $|d_1-d_2|/d_2$ is equal to or lower than $2.1\times10^{-3}$. Owing to the fact that the uniform distortion at the surface layer of the nitride crystal satisfies the relationship of $|d_1-d_2|/d_2 \leq 2.1\times10^{-3}$, a semiconductor layer of good crystallinity can be epitaxially grown on the nitride crystal, and a semiconductor device of good characteristics can be produced.

Second Embodiment

A nitride crystal of this embodiment is characterized in that, on a diffraction intensity profile of arbitrary specific parallel crystal lattice planes of the crystal obtained from X-ray diffraction measurement performed with variation of X-ray penetration depth from a surface of the crystal while X-ray diffraction conditions of the specific parallel crystal lattice planes are satisfied, an irregular distortion at a surface layer of the crystal represented by a value of $|v_1-v_2|$ obtained from a half value width $v_1$ of a diffraction intensity peak at the X-ray penetration depth of 0.3 μm and a half value width $v_2$ of the diffraction intensity peak at the X-ray penetration depth of 5 μm is equal to or lower than 150 arcsec.

Figure 4:
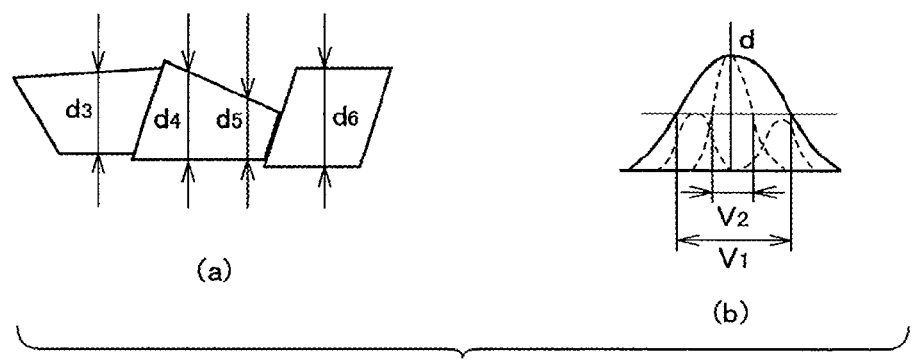
FIG. 4 schematically illustrates a relationship between irregular distortion of a crystal lattice of a nitride crystal and a half value width of a diffraction peak on a diffraction profile in the X-ray diffraction method. At (a), the irregular distortion of the crystal lattice is illustrated. At (b), the half value width of the diffraction peak on the diffraction profile is illustrated.

Referring to FIG. 1, the X-ray penetration depth of 0.3 μm corresponds to a distance from the surface of the nitride crystal to an inside of crystal surface layer 1$a$, and the X-ray penetration depth of 5 μm corresponds to a distance from the surface of the nitride crystal to an inside of crystal inner layer 1$c$. Referring to FIG. 4($a$), half value width $v_2$ of the diffraction peak at the X-ray penetration depth of 5 μm can be considered as the half value width of the nitride crystal in the original state, but half value width $v_1$ of the diffraction peak at the X-ray penetration depth of 0.3 μm reflects the irregular distortion of the crystal lattice at the crystal surface layer due to an influence of surface working of the crystal (e.g., different plane spacings $d_3$, $d_4$-$d_5$, $d_6$ of the respective crystal lattice planes), and therefore takes a value different from half value width $v_2$ of the diffraction peak at the X-ray penetration depth of 5 μm.

Referring to FIG. 4($b$), half value width $v_1$ of the diffraction peak at the X-ray penetration depth of 0.3 μm and half value width $v_2$ of the diffraction peak at the X-ray penetration depth of 5 μm appear on the diffraction profile relating to the arbitrary specific parallel crystal lattice planes of the crystal in the above case. Therefore, the irregular distortion of the crystal surface layer can be expressed by the value of $|v_1-v_2|$ which is a difference between $v_1$ and $v_2$.

In the nitride crystal of this embodiment, the irregular distortion at the surface layer represented by the value of $|v_1-v_2|$ is equal to or lower than 150 arcsec. Owing to the fact that the irregular distortion at the surface layer of the nitride crystal satisfies the relationship of $|v_1-v_2| \leq 150$ (arcsec), a semiconductor layer of good crystallinity can be epitaxially grown on the nitride crystal, and a semiconductor device of good characteristics can be produced.

Third Embodiment

A nitride crystal of this embodiment is characterized in that, on a rocking curve measured by varying an X-ray penetration depth from a crystal surface in connection with X-ray diffraction of arbitrary specific parallel crystal lattice planes of the crystal, a plane orientation deviation of the specific parallel crystal lattice planes represented by a value of $|w_1-w_2|$ obtained from a half value width $w_1$ of a diffraction intensity peak at the X-ray penetration depth of 0.3 μm and a half value width $w_2$ of the diffraction intensity peak at the X-ray penetration depth of 5 μm is equal to or lower than 400 arcsec.

Figure 5:
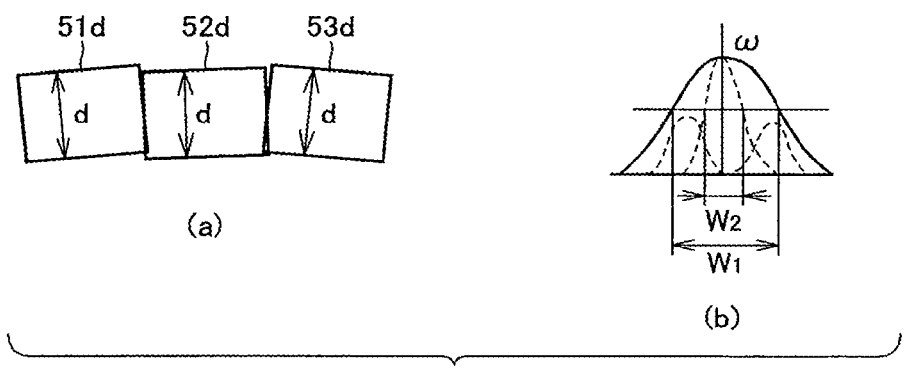
FIG. 5 schematically illustrates a relationship between plane orientation distortion of specific parallel crystal lattice planes of a nitride crystal and a half value width on a rocking curve in the X-ray diffraction method. At (a), the plane orientation deviation of the specific parallel crystal lattice planes is illustrated. At (b), the half value width of the diffraction peak on the rocking curve is illustrated.

Referring to FIG. 1, the X-ray penetration depth of 0.3 μm corresponds to a distance from the surface of the nitride crystal to an inside of crystal surface layer 1a, and the X-ray penetration depth of 5 μm corresponds to a distance from the surface of the nitride crystal to an inside of crystal inner layer 1c. Referring to FIG. 5(a), half value width $w_2$ at the X-ray penetration depth of 5 μm can be considered as the half value width of the crystal in the original state, but half value width $w_1$ at the X-ray penetration depth of 0.3 μm reflects the plane orientation deviation of the crystal lattice at the crystal surface layer due to an influence of surface working of the crystal (e.g., different plane orientation of respective specific parallel crystal lattice planes 51d, 52d and 53d of each crystal region), and therefore takes a value different from half value width $w_2$ at the X-ray penetration depth of 5 μm.

Referring to FIG. 5(b), half value width $w_1$ at the X-ray penetration depth of 0.3 μm and half value width $w_2$ at the X-ray penetration depth of 5 μm appear on the rocking curve relating to the arbitrary specific parallel crystal lattice planes of the crystal in the above case. Therefore, the plane direction deviation of the specific parallel crystal lattice planes of the crystal surface layer can be expressed by the value of $|w_1-w_2|$ which is a difference between $w_1$ and $w_2$.

In the nitride crystal of this embodiment, the plane orientation deviation of the specific parallel crystal lattice planes of the surface layer represented by the value of $|w_1-w_2|$ is equal to or lower than 400 arcsec. Owing to the fact that the plane orientation deviation of the specific parallel crystal lattice planes of the surface layer of the nitride crystal satisfies the relationship of $|w_2-w_2| \leq 400$ (arcsec), a semiconductor layer of good crystallinity can be epitaxially grown on the nitride crystal, and a semiconductor device of good characteristics can be produced.

The crystallinity evaluated by the crystallinity evaluating methods of the first to third embodiments described above is not restricted to that affected by the surface working already described, and may include a distortion of the crystal and the like that occur when the crystal grows.

In the nitride crystals of the first to third embodiments already described, the surface of the crystal preferably has a surface roughness Ry of 30 nm or lower. Surface roughness Ry is a sum of a height from an average plane of a sampling portion to the highest peak thereof and a depth from the average plane to the lowest bottom, and this sampling portion is extracted from a roughness curved plane as a reference area measuring 10 μm per side (i.e., 10 μm×10 μm=100 μm$^2$) in a direction of its average plane. Owing to the fact that the nitride crystal has surface roughness Ry of 30 nm or lower, the semiconductor layer of good crystallinity can be epitaxially grown on the nitride crystal, and the semiconductor device of good characteristics can be produced.

In the nitride crystals of the first to third embodiments already described, the surface of the crystal preferably has a surface roughness Ra of 3 nm or lower. Surface roughness Ra is a value obtained by averaging, with a reference area, a sum of absolute values of deviations from an average plane of a sampling portion to a measurement curved surface, and this sampling portion is extracted from a roughness curved plane as a reference area measuring 10 μm per side in a direction of the average plane. Owing to the fact that the nitride crystal has surface roughness Ra of 3 nm or lower, the semiconductor layer of good crystallinity can be epitaxially grown on the nitride crystal, and the semiconductor device of good characteristics can be produced.

In the nitride crystals of the first to third embodiments already described, it is preferable that the surface of the crystal is parallel to a C-plane in a wurtzite structure. The C-plane represents {0001} plane and {000-1} plane. The surface of group nitride crystal is parallel to each of the above planes in the wurtzite structure or is nearly parallel (e.g., at an off angle lower than 0.05° between the surface of the nitride crystal and the C-plane in the wurtzite structure), whereby the semiconductor layer of good crystallinity can be epitaxially grown on the nitride crystal, and the semiconductor device of good characteristics can be produced.

In the nitride crystals of the first to third embodiments already described, it is preferable that the surface of the crystal forms an off angle in a range from 0.05° to 15° with respect to the C-plane in the wurtzite structure. Provision of the off angle of 0.05° or more can reduce defects at the semiconductor layer that is epitaxially grown on the nitride crystal. However, when the off angle exceeds 15°, a step or a difference in level is liable to occur. From the viewpoint of this, the preferable off angle is from 0.1° to 10°.

Fourth Embodiment

This embodiment is a nitride crystal substrate formed of the nitride crystal of the first to third embodiments already described. One or more semiconductor layer(s) are epitaxially grown on at least one of main surfaces of the nitride crystal substrate of the embodiment to provide an epilayer-containing nitride crystal substrate including the one or more semiconductor layer(s) that are the epitaxial layer(s) also referred to as the "epilayer(s)". In this case, the semiconductor layer can be epitaxially grown on the nitride crystal substrate when a lattice constant $k_0$ of the nitride crystal substrate (i.e., the lattice constant in an axis perpendicular to a crystal growth plane (this explanation is also true in the following description of this embodiment)) and a lattice constant k of the semiconductor layer satisfy a relationship of $(|k-k_0|/k) \leq 0.15$. It is preferable to satisfy a relationship of $(|k-k_0|/k) \leq 0.05$. From the viewpoint of this, the semiconductor layer is preferable a III group nitride layer.

Fifth Embodiment

This embodiment is a semiconductor device including one or more semiconductor layer(s) formed by epitaxial growth on at least one of main surface sides of the nitride crystal substrate of the above fourth embodiment or the above epilayer-containing nitride crystal substrate. In the semiconductor device thus obtained, since at least one of the uniform distortion, the irregular distortion and the plane orientation deviation of the surface layer of the nitride crystal used as the substrate is small, the semiconductor layer formed on at least one of the main surfaces of the nitride crystal substrate or the epilayer-containing nitride crystal substrate has good crystallinity, and good device characteristics can be obtained.

The foregoing matters related to the semiconductor layer of the fourth embodiment can also be applied to the semiconductor layer of this embodiment. More specifically, the semiconductor layer can be epitaxially grown on the nitride crystal substrate when lattice constant $k_0$ of the nitride crystal substrate (i.e., the lattice constant in an axis perpendicular to the crystal growth plane (this explanation is also true in the following description of this embodiment)) and lattice constant k of the semiconductor layer satisfy the relationship of $(|k-k_0|/k) \leq 0.15$. It is preferable to satisfy the relationship of $(|k-k_0|/k) \leq 0.05$. From the viewpoint of this, the semiconductor layer is preferable the III group nitride layer.

The semiconductor device of this embodiment may be a light-emitting element such as a light-emitting diode or a laser diode, an electronic element such as a rectifier, a bipolar transistor, a field-effect transistor or a HEMT (High Electron Mobility Transistor), a semiconductor sensor such as a temperature sensor, a pressure sensor, a radiation sensor or a visible-ultraviolet ray detector, or a SAW device (Surface Acoustic Wave device).

Sixth Embodiment

Figure 6:
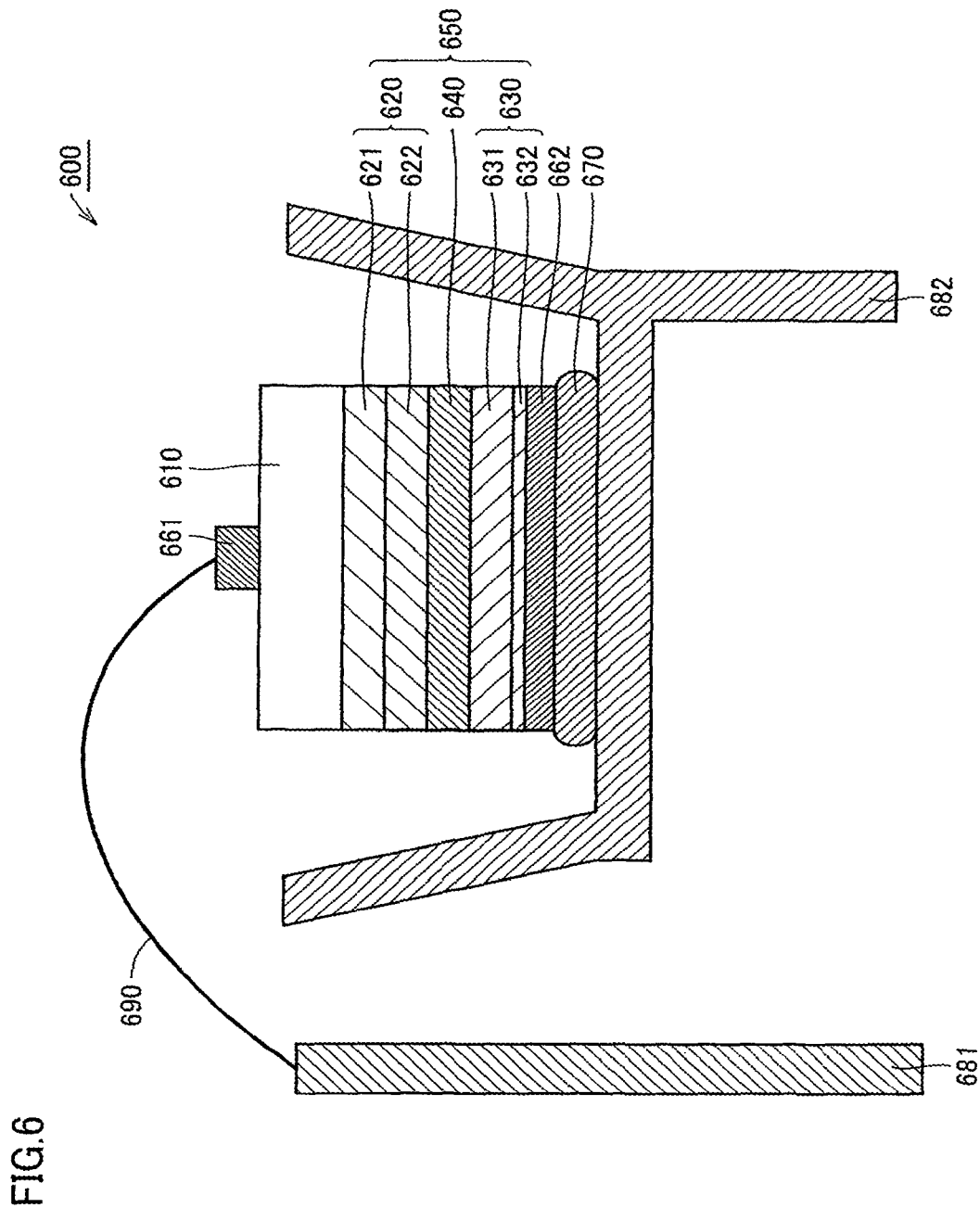
FIG. 6 is a schematic section showing an example of a semiconductor device according to the invention.

Referring to FIG. 6, a semiconductor device of this embodiment is a semiconductor device including the foregoing nitride crystal substrate or the epilayer-containing nitride crystal substrate as a substrate 610, and includes a light emitting element including a plurality of (i.e., three or more) semiconductor layers 650 formed by the epitaxial growth on one of the main surface sides of the nitride crystal substrate or the epilayer-containing nitride crystal substrate (substrate 610), a first electrode 661 formed on the other main surface side of the nitride crystal substrate or the epilayer-containing nitride crystal substrate (substrate 610), and a second electrode 662 formed on the outermost semiconductor layer of the plurality of semiconductor layers 650. The semiconductor device further includes a conductor 682 bearing the light emitting element. A side of the light emitting element defined by substrate 610 is a light emitting side, and a side defined by the outermost semiconductor layer side is a mount side. The plurality of semiconductor layers 650 include a p-type semiconductor layer 630, an n-type semiconductor layer 620 and a light emitting layer 640 formed between these conductive semiconductor layers. Owing to the above structure, it is possible to form the semiconductor device of which nitride crystal substrate side is the light emitting side.

The semiconductor device of this embodiment has a good property of releasing heat generated by a light emitting layer as compared with a semiconductor device of which semiconductor layer side is the light emitting side. Therefore, even in the operation with a high power, temperature rising of the semiconductor device is suppressed, and light emission at high brightness can be achieved. An insulating substrate such as a sapphire substrate must have a single-side electrode structure in which two kinds of electrodes, i.e., n- and p-electrodes are formed on the semiconductor layer. However, the semiconductor device of this embodiment can have a double-sided electrode structure in which the electrodes are formed on the semiconductor layer and the substrate, respectively, and a major portion of the main surface of the semiconductor device can be used as a light emitting surface. Further, when mounting the semiconductor device, the manufacturing process can be simple, e.g., because wire boding is required only one time. This advantage and the like can also be achieved.

Seventh Embodiment

This embodiment is a method of manufacturing a semiconductor device including a nitride crystal substrate or an epilayer-containing nitride crystal substrate including one or more semiconductor layer(s) formed by epitaxial growth on at least one of main surface sides of the nitride crystal substrate. This method of manufacturing the semiconductor device includes the steps of selecting the nitride crystal of the first embodiment as the nitride crystal substrate, and epitaxially growing the one or more semiconductor layer(s) on at least one of the main surface sides of the substrate.

Since the nitride crystal of the first embodiment selected as the nitride crystal substrate of the semiconductor device of the seventh embodiment has the surface layer of which uniform distortion is small, the semiconductor layer of good crystallinity can be epitaxially grown on the nitride crystal, and the semiconductor device of good characteristics can be formed. The foregoing matters related to the semiconductor layers of the fourth and fifth embodiments can be applied to the semiconductor layer of the seventh embodiment.

Eighth Embodiment

This embodiment is a method of manufacturing a semiconductor device including a nitride crystal substrate or an epilayer-containing nitride crystal substrate including one or more semiconductor layer(s) formed by epitaxial growth on at least one of main surface sides of the nitride crystal substrate. This method of manufacturing the semiconductor device includes the steps of selecting the nitride crystal of the second embodiment as the nitride crystal substrate, and epitaxially growing one or more semiconductor layer(s) on at least one of main surface sides of the substrate.

Since the nitride crystal of the second embodiment selected as the nitride crystal substrate of the semiconductor device of the eighth embodiment has the surface layer of which irregular distortion is small, the semiconductor layer of good crystallinity can be epitaxially grown on the nitride crystal, and the semiconductor device of good characteristics can be formed. The foregoing matters related to the semiconductor layers of the fourth and fifth embodiments can be applied to the semiconductor layer of the eighth embodiment.

Ninth Embodiment

This embodiment is a method of manufacturing a semiconductor device including a nitride crystal substrate or an epilayer-containing nitride crystal substrate including one or more semiconductor layer(s) formed by epitaxial growth on at least one of main surface sides of the nitride crystal substrate. This method of manufacturing the semiconductor device includes the steps of selecting the nitride crystal of the third embodiment as the nitride crystal substrate, and epitaxially growing one or more semiconductor layer(s) on at least one of main surface sides of the substrate.

Since the nitride crystal of the third embodiment selected as the nitride crystal substrate of the semiconductor device of the ninth embodiment includes the surface layer having specific parallel crystal lattice planes of which plane orientation deviation is small, the semiconductor layer of good crystallinity can be epitaxially grown on the nitride crystal, and the semiconductor device of good characteristics can be formed. The foregoing matters related to the semiconductor layers of the fourth and fifth embodiments can be applied to the semiconductor layer of the ninth embodiment.

The nitride crystal can be grown by a vapor phase growth method such as a HYPE (Hydride Vapor Phase Epitaxy) method or a sublimation method, or a liquid phase growth method such as a flux method.

A nitride crystal that will form the nitride crystal substrate of the semiconductor device is cut from the nitride crystal obtained by the foregoing growth method, and surface working such as grinding and polishing is performed for smoothing the surfaces thereof. In the mechanical working such as grinding and mechanical polishing included in the above surface working, hard grains cut into the crystal to remove the material so that work-affected layer (damaged layer) having deteriorated crystallinity is left at the surface of the nitride crystal that will form the nitride crystal substrate. Therefore, the work-affected layer must be reduced for producing the III group nitride semiconductor layer on the substrate smoothed by the mechanical working. The CMP processing is most suitable for reducing the work-affected layer because it can reduce both the work-affected layer and the surface roughness.

It is not necessary to remove completely the work-affected layer at the substrate surface, and the surface quality can be improved by annealing processing before the epitaxial growth. The annealing before the growth causes rearrangement at the crystal surfaces, and allows the epitaxial growth of the semiconductor layer of good crystallinity.

As a preferred example of the surface processing method for improving the crystallinity of the surface layer of the nitride crystal, the CMP surface treatment method will now be described. It is preferable that a value x of pH and a value y (mV) of an oxidation-reduction potential in a slurry solution used in the CMP satisfy both the following equations (2) and (3):

$$y \geq -50x + 1000 \quad (2)$$

$$y \leq -50x + 1900 \quad (3)$$

In the case of y<−50x+1000, a polishing speed becomes low. In the case of y>−50x+1900, a polishing pad and a polishing device are subjected to a large corrosion effect so that stable polishing becomes difficult.

From the viewpoint of further improving the polishing speed, it is further preferable to satisfy additionally the following equation (4):

$$y \geq -50x + 1300 \quad (4)$$

The slurry of the CMP usually contains an acid such as hydrochloric acid, sulfuric acid or nitric acid, and/or an alkali such as KOH or NaOH that are added thereto. However, the effect of oxidizing the surface of the chemically stable gallium nitride is small when such acid and/or alkali are used alone. Accordingly, it is preferable to increase the oxidation-reduction potential by adding an oxidizer so that the relationships of the foregoing equations (2) and (3), or the foregoing equations (3) and (4) may be satisfied.

The oxidizer added to the slurry of the CMP is not particularly restricted, but is preferably selected from among chlorinated isocyanuric acids such as trichloroisocyanuric acid, chlorinated isocyanurates such as sodium dichloroisocyanurate, permanganates such as potassium permanganate, dichromates such as potassium dichromate, bromates such as potassium bromate, thiosulfates such as sodium thiosulfate, hypochlorous acid, nitrates, hydrogen peroxide solutions and ozone. Each of these oxidizers may be used alone, or two or more of them may be used in combination.

It is preferable that the pH of slurry of the CMP is 6 or lower, or 8 or more. Acidic slurry having a pH of 6 or lower, or basic slurry having a pH of 8 or more is brought into contact with the III group nitride crystal to etch and remove the work-affected layer of the III group nitride crystal so that the polishing speed can be increased. From the viewpoint of this, it is more preferable that the pH of slurry is 4 or lower, or 10 or higher.

The acid and base used for controlling the pH of slurry are not particularly restricted, and may be selected, e.g., from among inorganic acids such as hydrochloric acid, nitric acid, sulfuric acid and phosphoric acid, organic acids such as formic acid, acetic acid, citric acid, malic acid, tartaric acid, succinic acid, phthalic acid and fumaric acid, bases such as KOH, NaOH and NH$_4$OH and amine, and salts such as sulfate, carbonate and phosphate. Also, the pH can be controlled by addition of the above oxidizer.

The slurry of the CMP preferably contains grains. These grains can increase the polishing speed. The grains contained in the slurry are not particularly restricted, and may be hard grains having a higher hardness than the nitride crystal, soft grains having a lower hardness than the nitride crystal, or grain mixtures of the hard and soft grains.

Comparative Example 1

An n-type MN crystal of 500 μm in thickness that was grown by the HYPE method and was doped with Si was used as the nitride crystal, and was mechanically polished as follows. A Ga-side C-plane ((0001) plane) of the n-type GaN crystal having a diameter of 50 mm and a thickness of 500 μm was pressed against a surface table of a lapping apparatus while supplying slurry containing diamond grains in a dispersed fashion onto the surface table, and thereby the n-type GaN crystal was mechanically polished. The surface table was a copper or tin surface table. Three kinds of grains having different diameters of 6 μm, 3 μm and 1 μm, respectively, were prepared, and the grain diameters of the grains to be used were lowered stepwise in accordance with progress of the mechanical polishing. However, the polishing pressure in the mechanical polishing was from 100 gf/cm$^2$ to 500 gf/cm$^2$, and a rotation speed of the surface table was from 30 rpm to 100 rpm.

Then, measuring processing was effected on the n-type GaN crystal subjected to the mechanical polishing to measure diffraction X-rays from (10-13) planes of the wurtzite structure while changing the X-ray penetration depth from 0.3 μm to 5 μm, and thereby to obtain a plane spacing of the (10-13) planes (the specific parallel crystal lattice planes in this measurement) and a half value width of a diffraction intensity peak on a diffraction profile as well as a half value width of a diffraction intensity peak on a rocking curve. A parallel optical system and an X-ray wavelength of CuK$_{\alpha 1}$ were used for the X-ray diffraction measurement. The X-ray penetration depth was controlled by changing at least one of X-ray incident angle ω to the crystal surface, inclination angle χ of the crystal surface and rotary angle of φ within the crystal surface. Surface roughness Ry and surface roughness Ra of this n-type GaN crystal were measured with an AFM (Atomic Force Microscope: DIMENSION N3100 manufactured by VEECO Corp). The result is represented in a table 1.

Referring to FIG. 6, an n-type GaN layer 621 (dopant: Si) of 1 μm in thickness forming n-type semiconductor layer 620, an n-type Al$_{0.1}$Ga$_{0.9}$N layer 622 (dopant: Si) of 150 nm in thickness also forming n-type semiconductor layer 620, light emitting layer 640, a p-type Al$_{0.2}$Ga$_{0.8}$N layer 631 (dopant: Mg) of 20 nm in thickness forming p-type semiconductor layer 630 and a p-type GaN layer 632 (dopant: Mg) of 150 nm in thickness also forming p-type semiconductor layer 630 were successively formed by a MOCVD method on one of the main surface sides of substrate 610 of the n-type GaN crystal, thereby obtaining epitaxially-grown-layers for a light emitting element. Light emitting layer 640 had a multiple quantum-well structure in which four barrier layers formed of GaN layers each having a thickness of 10 nm and three well layers formed of $Ga_{0.85}In_{0.15}N$ layers each having a thickness of 3 nm were layered alternately.

A layered structure formed of a Ti layer of 200 nm in thickness, an Al layer of 1000 nm in thickness, a Ti layer of 200 nm in thickness and an Au layer of 2000 nm in thickness is formed as first electrode 661 on the other main surface side of substrate 610 of the n-type GaN crystal, and was heated in a nitrogen atmosphere to form an n-side electrode of 100 μm in diameter. Also, a layered structure formed of an Ni layer of 4 nm in thickness and an Ai layer of 4 nm in thickness was formed as second electrode 662 on p-type GaN layer 632, and was heated in an inert gas atmosphere to form a p-side electrode. A chip measuring 400 μm per side was prepared from the above layered structure, and then the above p-side electrode was bonded to conductor 682 with a solder layer 670 made of AuSn. Further, the n-side electrode and a conductor 681 were bonded together with a wire 690 so that a semiconductor device 600 having a structure as the light emitting device was obtained. The semiconductor device thus obtained was arranged in an integrating sphere. Then, a current of 20 mA is supplied to the semiconductor device to emit light, and the output of light gathered by the integrating sphere was measured. However, light emission from the semiconductor device of this comparative example was not confirmed. The result is represented in the table 1.

Examples 1-7

Semiconductor devices were produced under the same conditions as those of the comparative example 1 except for that CMP was performed under the conditions described in the table 1 after the mechanical polishing and before the X-ray diffraction. Light outputs of the produced semiconductor devices were measured similarly to the comparative example 1. The result is represented in the table 1.

TABLE 1

| | | COMPARATIVE EXAMPLE 1 | EXAMPLE 1 | EXAMPLE 2 | EXAMPLE 3 | EXAMPLE 4 | EXAMPLE 5 | EXAMPLE 6 | EXAMPLE 7 |
|---|---|---|---|---|---|---|---|---|---|
| CMP | pH OF SLURRY | NO CMP | 9.5 | 2.4 | 3.5 | 3.5 | 3.5 | 3.5 | 3.0 |
| | OXIDATION-REDUCTION POTENTIAL OF SLURRY (mV) | | 980 | 1420 | 1200 | 1200 | 1200 | 1200 | 1200 |
| | OXIDIZER | | Na-DCIA | TCIA | TCIA | TCIA | TCIA | TCIA | TCIA |
| | HARD GRAIN | | — | — | $Al_2O_3$ | $Al_2O_3$ | $Al_2O_3$ | $Al_2O_3$ | $Cr_2O_3$ |
| | GRAIN DIAMETER (μm) | | — | — | 0.5 | 1.0 | 2.0 | 0.5 | 0.8 |
| | SOFT GRAIN | | $SiO_2$ | $SiO_2$ | — | — | — | $SiO_2$ | $SiO_2$ |
| | MIXTURE VOLUME RATIO ((HARD GRAINS):(SOFT GRAINS)) | | — | — | — | — | — | 10:90 | 10:90 |
| | POLISHING RATE (μm/hr) | | 0.4 | 0.5 | 1.1 | 1.6 | 1.9 | 0.8 | 1.5 |
| CHARACTERISTICS | $\mid d_1 - d_2 \mid / d_2$ | $2.3 \times 10^{-3}$ | $0.3 \times 10^{-3}$ | $0.3 \times 10^{-3}$ | $1.0 \times 10^{-3}$ | $1.7 \times 10^{-3}$ | $2.1 \times 10^{-3}$ | $0.6 \times 10^{-3}$ | $1.4 \times 10^{-3}$ |
| | $\mid v_1 - v_2 \mid$ (arcsec) | 290 | 60 | 50 | 90 | 130 | 150 | 80 | 110 |
| | $\mid w_1 - w_2 \mid$ (arcsec) | 500 | 130 | 120 | 220 | 340 | 400 | 190 | 300 |
| | SURFACE ROUGHNESS Ry (nm) | >100 | 1.8 | 1.0 | 4.1 | 5.3 | 8.9 | 2.9 | 4.8 |
| | SURFACE ROUGHNESS Ra (nm) | >10 | 0.15 | 0.09 | 0.42 | 0.51 | 0.85 | 0.26 | 0.45 |
| | LIGHT OUTPUT (mW) | — | 15.6 | 16.4 | 12.3 | 9.8 | 8.2 | 13.9 | 10.7 |

(NOTE)
NA-DCIA: SODIUM DICHLOROISOCYANURATE, TCIA: TRICHLOROISOCYANURIC ACID

Comparative Example 2

An n-type AlN crystal of 400 μm in thickness that was grown by the sublimation method and was doped with Si was used as the nitride crystal, and was mechanically polished similarly to the comparative example 1.

Then, measuring processing was effected on the n-type AlN crystal subjected to the mechanical polishing to measure diffraction X-rays from (11-22) planes of the wurtzite structure while changing the X-ray penetration depth from 0.3 μm to 5 μm, and thereby to obtain a place spacing of the (11-22) planes (specific parallel crystal lattice planes in this measurement) and a half value width of a diffraction intensity peak on a diffraction profile as well as a half value width of the diffraction intensity peak on a rocking curve. A parallel optical system and an X-ray wavelength of $CuK_{\alpha 1}$ were used for the X-ray diffraction measurement. The X-ray penetration depth was controlled by changing at least one of X-ray incident angle ω to the crystal surface, inclination angle χ of the crystal surface and rotary angle of φ within the crystal surface. Surface roughness Ry and surface roughness Ra of this n-type AlN crystal were measured with the AFM. The result is represented in a table 2.

A semiconductor device using the above AlN crystal as a substrate was produced similarly to the comparative example 1. A light output of the semiconductor device thus produced was measured similarly to the comparative example 1. Light emission was not confirmed. The result is represented in the table 2.

Examples 8-10

Semiconductor devices were produced under the same conditions as those of the comparative example 2 except for that CMP was performed under the conditions described in the table 2 after the mechanical polishing and before the X-ray diffraction. The result is represented in the table 2.

TABLE 2

| | | COMPARATIVE EXAMPLE 2 | EXAMPLE 8 | EXAMPLE 9 | EXAMPLE 10 |
|---|---|---|---|---|---|
| CMP | pH OF SLURRY | NO CMP | 9.5 | 2.4 | 3.5 |
| | OXIDATION-REDUCTION POTENTIAL OF SLURRY (mV) | | 980 | 1420 | 1200 |
| | OXIDIZER | | Na-DCIA | TCIA | TCIA |
| | HARD GRAIN | | — | — | $Al_2O_3$ |
| | GRAIN DIAMETER (μm) | | — | — | 0.5 |
| | SOFT GRAIN | | $SiO_2$ | $SiO_2$ | — |
| | MIXTURE VOLUME RATIO ((HARD GRAINS):(SOFT GRAINS)) | | — | — | — |
| | POLISHING RATE (μm/hr) | | 0.6 | 0.8 | 1.4 |
| CHARACTERISTICS | $|d_1 - d_2|/d_2$ | $2.4 \times 10^{-3}$ | $0.5 \times 10^{-3}$ | $0.4 \times 10^{-3}$ | $1.4 \times 10^{-3}$ |
| | $|v_1 - v_2|$ (arcsec) | 310 | 80 | 70 | 110 |
| | $|w_1 - w_2|$ (arcsec) | 510 | 140 | 130 | 220 |
| | SURFACE ROUGHNESS Ry (nm) | >100 | 1.0 | 1.4 | 4.5 |
| | SURFACE ROUGHNESS Ra (nm) | >10 | 0.09 | 0.12 | 0.41 |
| | LIGHT OUTPUT (mW) | — | 13.9 | 14.8 | 10.9 |

(NOTE)
NA-DCIA: SODIUM DICHLOROISOCYANURATE
TCIA: TRICHLOROISOCYANURIC ACID

As is apparent from the foregoing tables 1 and 2, high light outputs were achieved by the LEDs that are the semiconductor devices each selectively employing, as the nitride crystal substrate, the nitride crystal satisfying the conditions that, in the X-ray diffraction measurement performed with variation of X-ray penetration depth from the crystal surface while X-ray diffraction conditions of the arbitrary specific parallel crystal lattice planes of the crystal are satisfied, the uniform distortion $|d_1-d_2|/d_2$ at the surface layer obtained from the plane spacing $d_1$ of the specific parallel crystal lattice planes at the X-ray penetration depth of 0.3 μm and the plane spacing $d_2$ of the specific parallel crystal lattice planes at the X-ray penetration depth of 5 μm is equal to or lower than $2.1 \times 10^{-3}$, the irregular distortion $|v_1-v_2|$ at the crystal surface layer obtained from the half value width $v_1$ of the diffraction intensity peak at the X-ray penetration depth of 0.3 μm and the half value width $v_2$ of the diffraction intensity peak at the X-ray penetration depth of 5 μm is equal to or lower than 150 arcsec, or the plane direction deviation $|w_1-w_2|$ of the specific parallel crystal lattice plane obtained from the half value width $w_1$ of the diffraction intensity peak at the X-ray penetration depth of 0.3 μm and the half value width $w_2$ of the diffraction intensity peak at the X-ray penetration depth of 5 μm is equal to or lower than 400 arcsec.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An n-type nitride crystal, wherein,
in connection with plane spacing of arbitrary specific parallel crystal lattice planes of the nitride crystal obtained from X-ray diffraction measurement performed with variation of X-ray penetration depth from a surface of said crystal while X-ray diffraction conditions of said specific parallel crystal lattice planes being satisfied, a uniform distortion at a surface layer of said crystal represented by a value of $|d_1-d_2|/d_2$ obtained from said plane spacing $d_1$ at said X-ray penetration depth of 0.3 μm and said plane spacing $d_2$ at the X-ray penetration depth of 5 μm is equal to or lower than $2.1 \times 10^{-3}$.

2. An n-type nitride crystal, wherein,
on a diffraction intensity profile of arbitrary specific parallel crystal lattice planes of the nitride crystal obtained from X-ray diffraction measurement performed with variation of X-ray penetration depth from a surface of said crystal while X-ray diffraction conditions of said specific parallel crystal lattice planes being satisfied, an irregular distortion at a surface layer of said crystal represented by a value of $|v_1-v_2|$ obtained from a half value width $v_1$ of a diffraction intensity peak at said X-ray penetration depth of 0.3 μm and a half value width $v_2$ of the diffraction intensity peak at said X-ray penetration depth of 5 μm is equal to or lower than 150 arcsec.

3. An n-type nitride crystal, wherein,
on a rocking curve measured by varying an X-ray penetration depth from a surface of the nitride crystal in connection with X-ray diffraction of arbitrary specific parallel crystal lattice planes of said crystal, a plane orientation deviation of said specific parallel crystal lattice planes represented by a value of $|w_1-w_2|$ obtained from a half value width $w_1$ of a diffraction intensity peak at said X-ray penetration depth of 0.3 μm and a half value width $w_2$ of the diffraction intensity peak at said X-ray penetration depth of 5 μm is equal to or lower than 400 arcsec.

4. The n-type nitride crystal according to claim 2, wherein said surface of said crystal has a surface roughness Ry of 30 nm or lower.

5. The n-type nitride crystal according to claim 2, wherein said surface of said crystal has a surface roughness Ra of 3 nm or lower.

6. The n-type nitride crystal according to claim 2, wherein said surface of said nitride crystal is parallel to a C-plane of a wurtzite structure.

7. The n-type nitride crystal according to claim 2, wherein said surface of said nitride crystal has an off angle in a range from 0.05° to 15° with respect to a C-plane of a wurtzite structure.

8. A Si-doped nitride crystal substrate formed of the n-type nitride crystal according to claim 2, wherein said n-type nitride crystal is an Si-doped nitride crystal.

\* \* \* \* \*